United States Patent [19]
Cillik

[11] Patent Number: 5,711,034
[45] Date of Patent: Jan. 27, 1998

[54] MENSTRUAL UNDERPANTS

[76] Inventor: Timea Cillik, 337 88th St., Brooklyn, N.Y. 11209

[21] Appl. No.: 778,752

[22] Filed: Jan. 6, 1997

[51] Int. Cl.⁶ ................................................ A41B 9/04
[52] U.S. Cl. ................................ 2/406; 604/392; 604/398
[58] Field of Search ........................... 2/400, 406, 919, 2/407, 409; 604/392, 385.1, 386, 393, 395, 397, 398, 402; 450/102–104; 602/67–73

[56] References Cited

U.S. PATENT DOCUMENTS

| 2,587,459 | 2/1952 | Fuentes | 604/398 |
| 3,108,599 | 10/1963 | Mammarella | 450/102 |
| 5,241,710 | 9/1993 | Lockhart . | |
| 5,255,392 | 10/1993 | Stanislaw . | |
| 5,325,543 | 7/1994 | Allen . | |
| 5,392,467 | 2/1995 | Moretz et al. . | |

FOREIGN PATENT DOCUMENTS

| 1227935 | 8/1960 | France | 604/398 |
| 743365 | 1/1956 | United Kingdom . | |
| 853467 | 11/1960 | United Kingdom | 604/398 |

*Primary Examiner*—Gloria Hale
*Attorney, Agent, or Firm*—Michael I. Kroll

[57] ABSTRACT

A menstrual underpants (12) comprising a garment (14) configured with a front portion (16), a rear portion (18), a crotch area (20), having two leg openings (22) and a waist opening (24), so as to be worn about a lower torso of a woman (26). Provision is made for engaging opposite ends (29) of an absorbent pad (30). A facility (32) is for securing the engaging structure (28) to the crotch area (20) of the garment (14). The absorbent pad (30) will be held in place at the crotch area (20) and not move up and down, while edges of the absorbent pad (30) will not curl up, to allow the woman (26) to have more comfort, when wearing the garment (14).

3 Claims, 4 Drawing Sheets

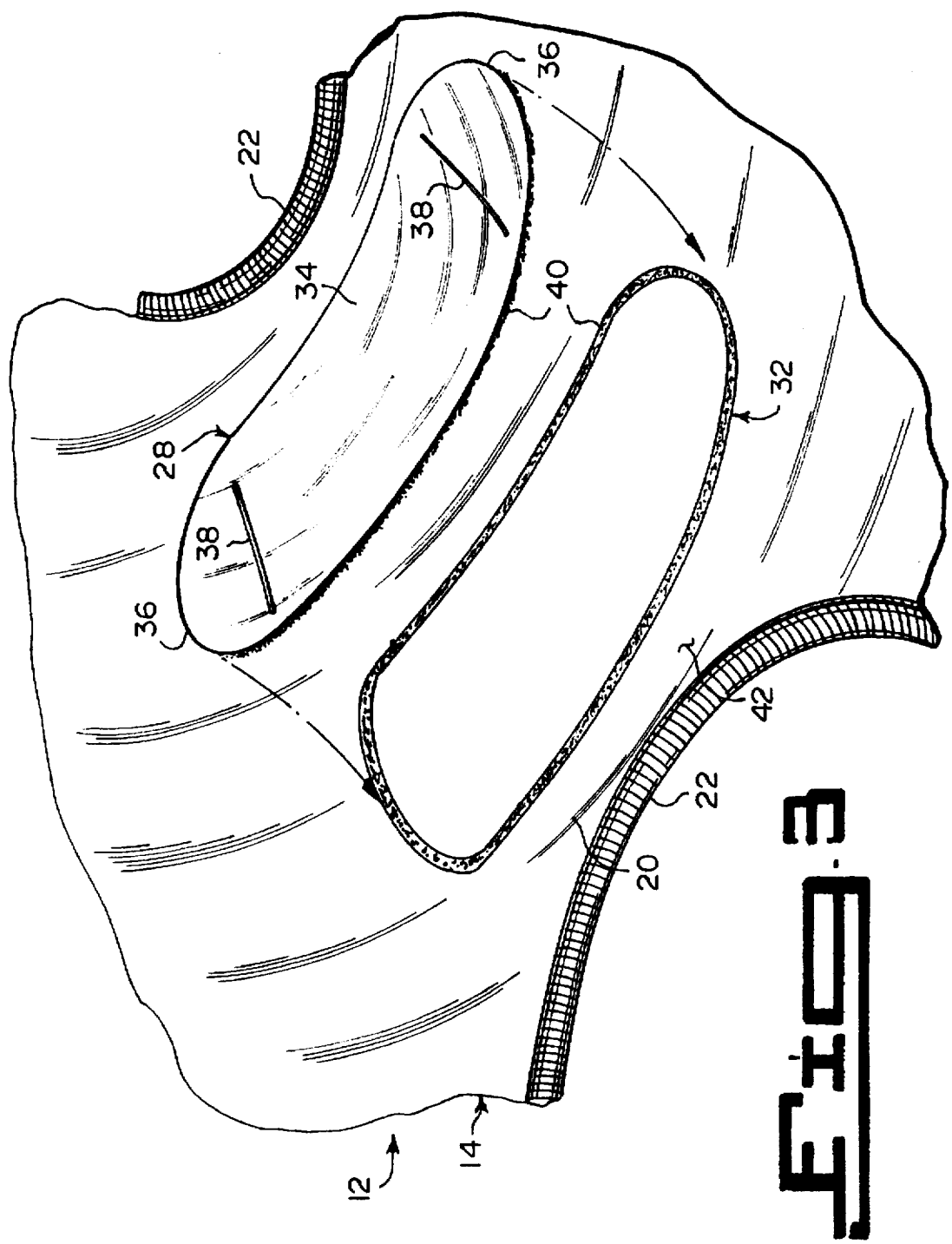

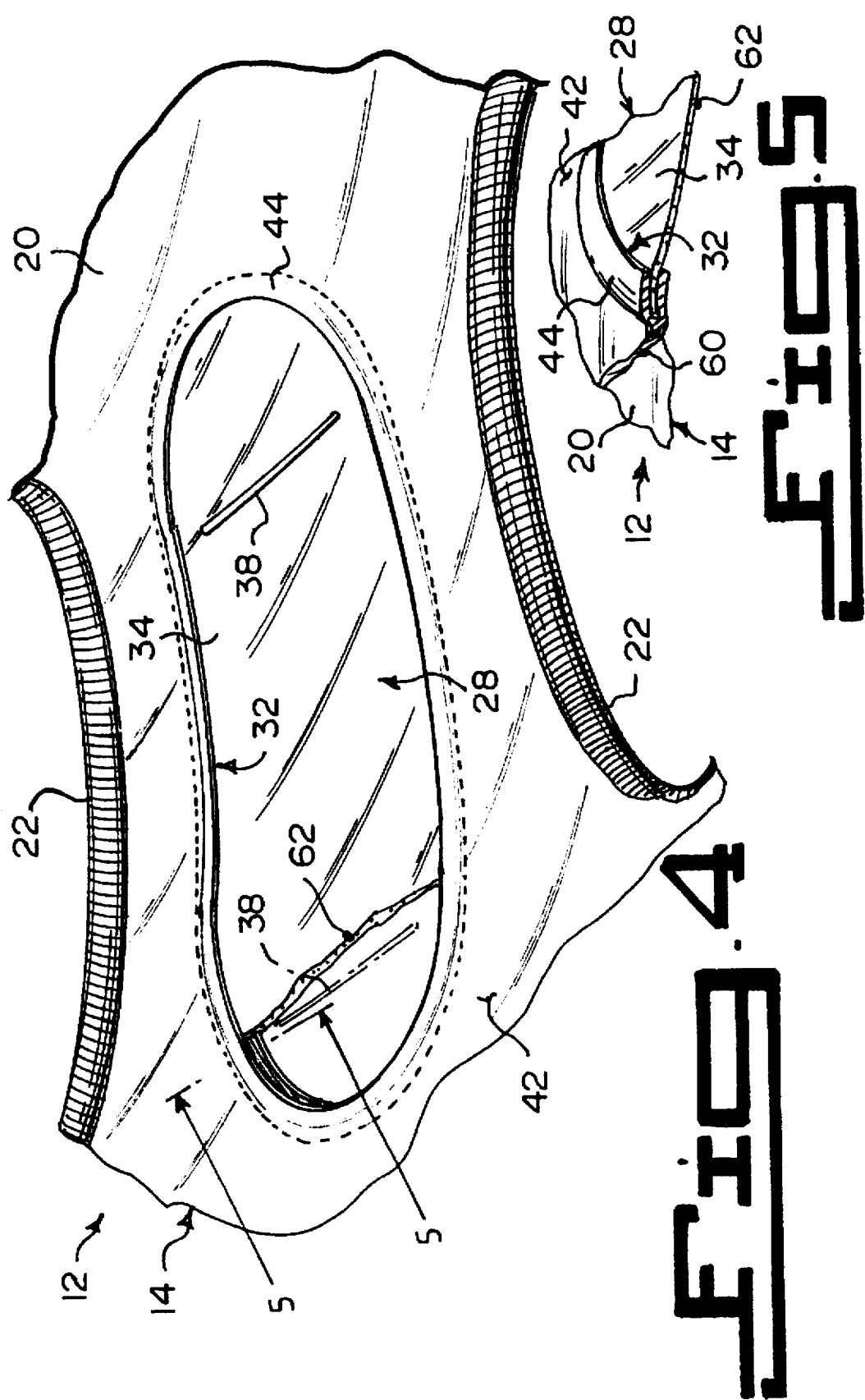

MENSTRUAL UNDERPANTS

BACKGROUND OF THE INVENTION

1. Field of the Invention

The instant invention relates generally to concealed pockets in garments and more specifically it relates to a menstrual underpants.

2. Description of the Prior Art

Numerous concealed pockets in garments have been provided in prior art. For example, U.S. Pat. No. 5,241,710 to Lockhart; U.S. Pat. No. 5,255,392 to Stanislaw; U.S. Pat. No. 5,325,543 to Allen and U.S. Pat. No. 5,392,467 to Moretz et al. all are illustrative of such prior art. While these units may be suitable for the particular purpose to which they address, they would not be as suitable for the purposes of the present invention as heretofore described.

LOCKHART, JANICE T.

SANITARY PANTY

U.S. Pat. No. 5,241,710

A two piece panty with one of the pieces being a removable lower or crotch portion. This portion has an inner section designed for the absorption of menses, and an outer moisture resistant backing that includes both a front and rear engaging means and a pocket adapted to hold a pre-wrapped moistened towelette. Thus, when the inner section become soiled, it is easily replaceable by disengaging the crotch portion and replacing it with a new one.

STANISLAW, THELMA E.

CONCEALED POCKET

U.S. Pat. No. 5,255,392

A concealed pocket assembly, and more particularly, a concealed pocket assembly which can be incorporated into swim wear, beach wear, active wear, exercise wear and related articles. The concealed pocket assembly is generally provided for incorporation into clothing. The concealed pocket assembly includes a pocket member attached to a fabric portion adjacent an edge of the opening of the pocket and in association with a lining portion of the garment.

ALLEN, TANYA R.

UNDERGARMENT WITH A POCKET FOR RELEASABLY SECURING AN ABSORBENT PAD

U.S. Pat. No. 5,325,543

A disposable undergarment for releasably securing an absorbent pad in a pocket located in the crotch portion of the undergarment and a method for making the same is disclosed. The undergarment is made with a body portion and pocket portion. The pocket portion overlays the crotch portion and is attached to the body portion along a sufficient portion of its peripheral edge to form a pocket therebetween. The pocket is sufficient in size to secure or store an absorbent pad or the like. Preferably, the undergarment is made of an inexpensive material, so that it may be disposable.

MORETZ, HERBERT L.

BRIER, DANIEL L.

MOISTURE-MANAGEMENT GARMENT AND SUPPORT POUCH GARMENT

A moisture-management garment and support garment including a moisture-management panel which extends from an upper crotch area of the garment to a lower crotch area of the garment. The panel includes an inner fabric layer, intermediate fabric layer, and an outer fabric layer. The inner fabric layer is constructed of wicking yarns for residing in skin contact during garment wear. The intermediate fabric layer comprises one or more moisture transport inserts which reside adjacent to the inner fabric layer for transporting moisture away from the inner fabric layer and away from the skin of the wearer. An outer fabric layer resides adjacent the intermediate fabric layer for receiving and dispensing moisture wicked outwardly from the inner and intermediate fabric layers.

SUMMARY OF THE INVENTION

A primary object of the present invention is to provide a menstrual underpants that will overcome the shortcomings of the prior art devices.

Another object is to provide a menstrual underpants that will hold an absorbent pad in place at a crotch area, so that the absorbent pad will not move up and down.

An additional object is to provide a menstrual underpants that will prevent the edges of the absorbent pad from curling up, thereby allowing a woman to have more comfort, especially to sleep without worrying that the absorbent pad may slide out of the crotch area.

A further object is to provide a menstrual underpants that is simple and easy to use.

A still further object is to provide a menstrual underpants that is economical in cost to manufacture.

Further objects of the invention will appear as the description proceeds.

To the accomplishment of the above and related objects, this invention may be embodied in the form illustrated in the accompanying drawings, attention being called to the fact, however, that the drawings are illustrative only, and that changes may be made in the specific construction illustrated and described within the scope of the appended claims.

BRIEF DESCRIPTION OF THE DRAWING FIGURES

Various other objects, features and attendant advantages of the present invention will become more fully appreciated as the same becomes better understood when considered in conjunction with the accompanying drawings, in which like reference characters designate the same or similar parts throughout the several views, and wherein;

FIG. 3 is an inner perspective view taken in the direction of arrow 3 in FIG. 2, showing the pocket exploded having a VELCRO fastener for attachment to the crotch area.

FIG. 4 is an inner perspective view taken in the direction of arrow 4 in FIG. 2 with parts broken away and in section, showing the pocket having a heat seal thereabout in the crotch area.

FIG. 5 is a cross sectional perspective view taken along line 5—5 in FIG. 4, showing the heat seal in greater detail.

Similar reference characters denote corresponding features consistently throughout the attached drawings.

DETAILED DESCRIPTION OF THE PREFERRED EMBODIMENTS

Figure 1:
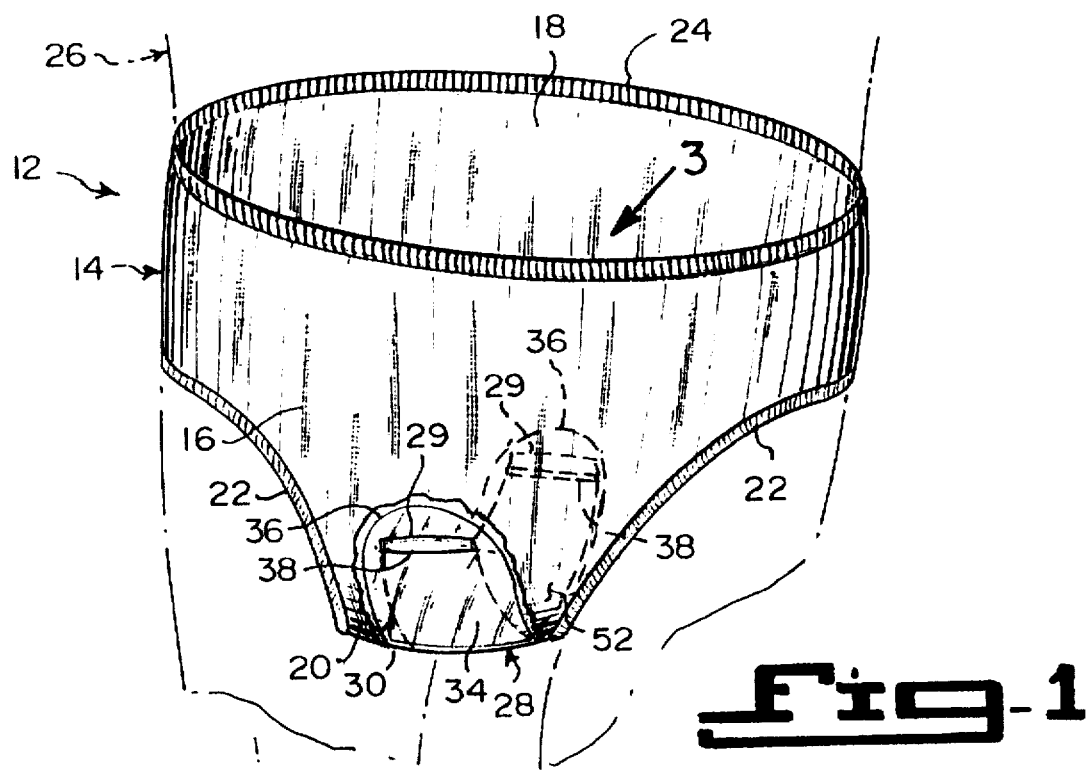
FIG. 1 is a front perspective view of a first embodiment of the instant invention with parts broken away.
Figure 2:
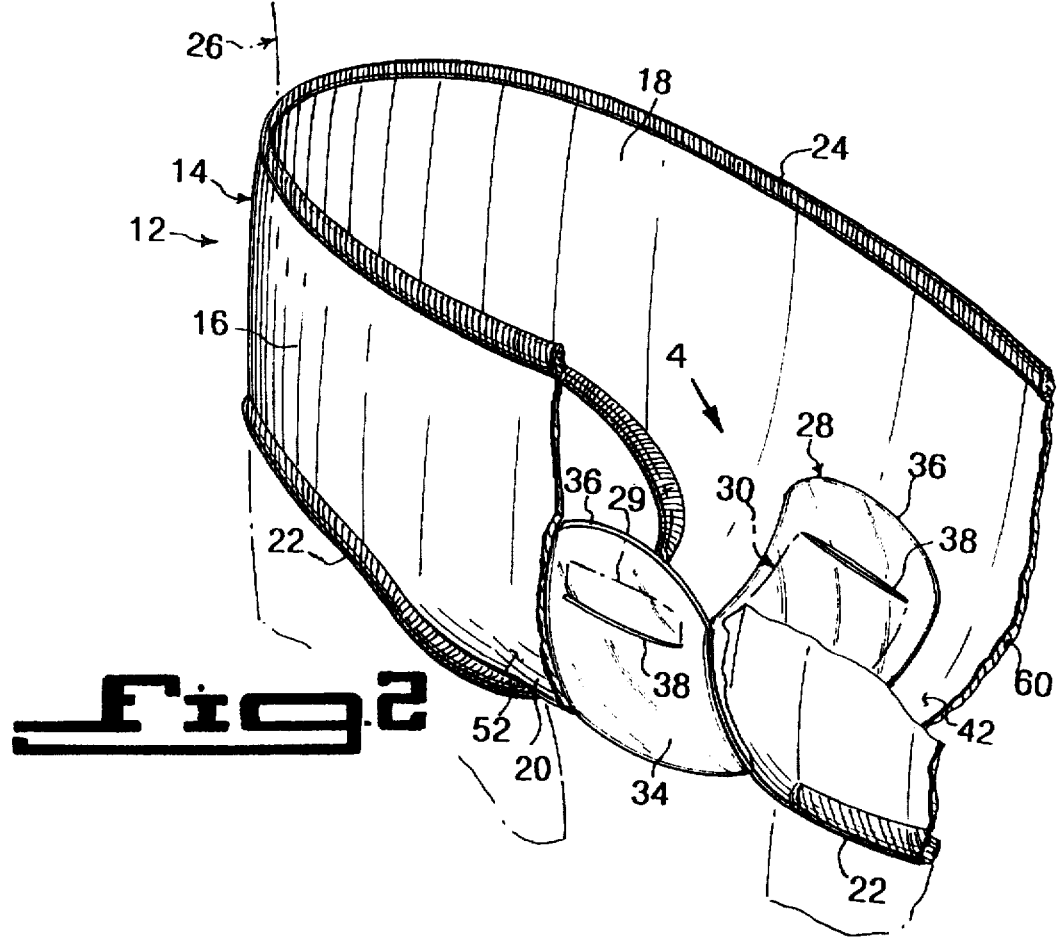
FIG. 2 is an enlarged front perspective view of the first embodiment with parts broken away and in section.

Turning now descriptively to the drawings, in which similar reference characters denote similar elements throughout the several views, FIGS. 1 through 11 illustrate a menstrual underpants 12 comprising a garment 14 configured with a front portion 16, a rear portion 18, a crotch area 20, having two leg openings 22 and a waist opening 24, so as to be worn about a lower torso of a woman 26. A structure 28 is for engaging opposite ends 29 of an absorbent pad 30. A facility 32 is for securing the engaging structure 28 to the crotch area 20 of the garment 14. The absorbent pad 30 will be held in place at the crotch area 20 and not move up and down, while edges of the absorbent pad 30 will not curl up, to allow the woman 26 to have more comfort, when wearing the garment 14.

The engaging structure 28, as shown in FIGS. 1 through 5, is a flexible pocket 34 having rounded ends 36 with a pair of transverse slot openings 38. Each transverse slot opening 38 is spaced away from each rounded end 36, so that opposite ends 29 of the absorbent pad 38 can be inserted through the transverse slot openings 38.

The securing facility 32, as shown in FIG. 3, is mating hook and loop pile fastener material 40 about the perimeter of the elongated flexible pocket 34 and an interior surface 42 of the crotch area 20 of the garment 14. The securing facility 32, as shown in FIGS. 4 and 5, is a heat seal 44 about the perimeter of the elongated flexible pocket 34 and an interior surface 42 of the crotch area 20 of the garment 14.

Figure 6:
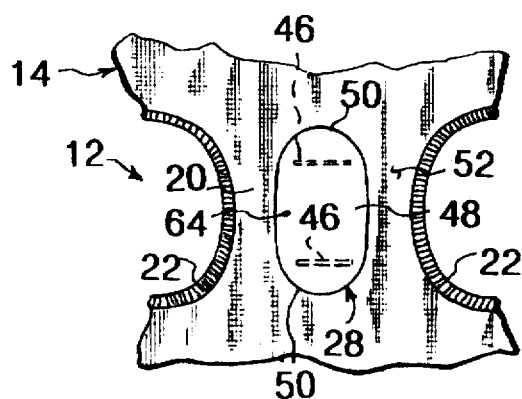
FIG. 6 is a bottom flat plan view of a second embodiment of the instant invention with parts broken away.
Figure 7:
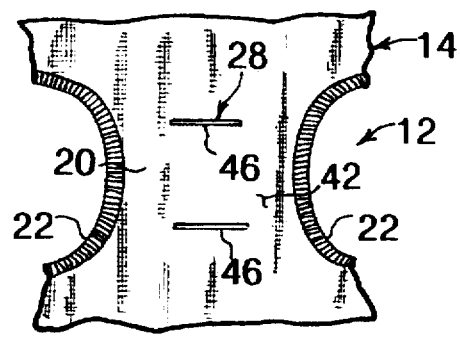
FIG. 7 is a top flat plan view of the second embodiment with parts broken away and the absorbent pad removed from the crotch area.

The engaging structure 28, as shown in FIGS. 6 and 7, includes the crotch area 20 of the garment 14 having two spaced apart transverse slot openings 46. Opposite end 29 of the absorbent pad 30 can be inserted through the transverse slot openings 46 on an interior surface 42 of the crotch area 20. An elongated flexible pocket 48 having rounded ends 50 is provided. The securing facility 32 will attach the elongated flexible pocket 48 to an exterior surface 52 of the crotch area 20 over the transverse slot openings 46, and cover the opposite ends 29 of the absorbent pad 30 extending through the transverse slot openings 46 in the crotch area 20.

Figure 8:
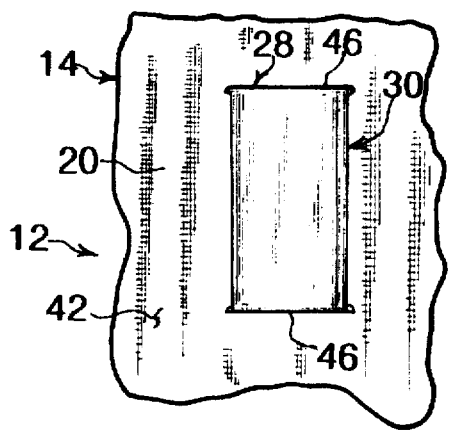
FIG. 8 is a top flat plan view of a third embodiment of the instant invention with parts broken away and the absorbent pad in place at the crotch area.
Figure 9:
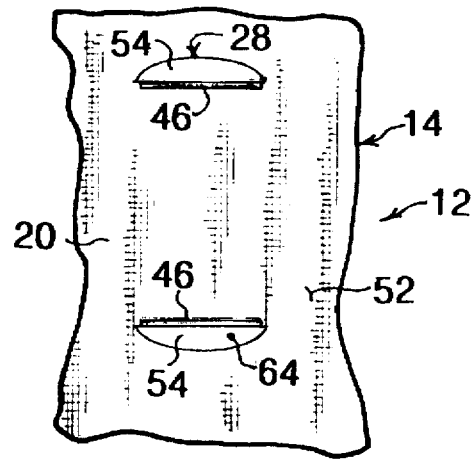
FIG. 9 is a bottom flat plan view of the third embodiment with parts broken away.

The engaging structure 28 in FIGS. 8 and 9, consists of the crotch area 20 of the garment having the two spaced apart transverse slot openings 46. Opposite ends 29 of the absorbent pad 30 can be inserted through the transverse slot openings 46 on the interior surface 42 of the crotch area 20. A pair of curved end pockets 54 are provided. The securing facility 32 will attach each curved end pocket 54 to the exterior surface 52 of the crotch area 20, adjacent one transverse slot opening 46. The opposite ends 29 of the absorbent pad 30 extending through the transverse slot openings 46 in the crotch area 20, will be received and retained within the curved end pockets 54.

Figure 10:
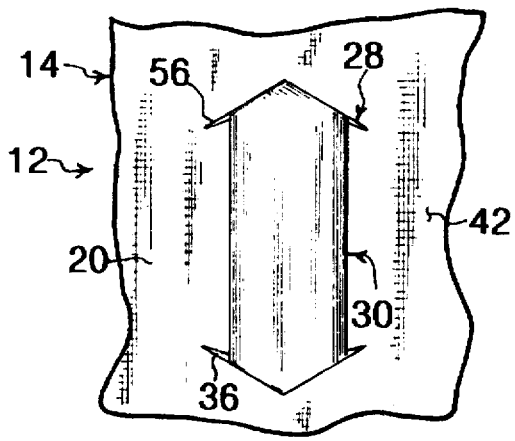
FIG. 10 is a top flat plan view of a fourth embodiment with parts broken away and the absorbent pad in place at the crotch area.
Figure 11:
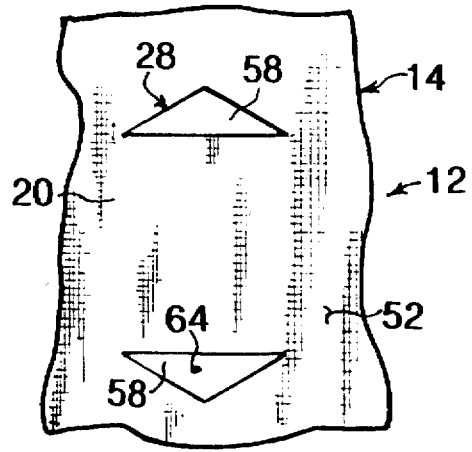
FIG. 11 is a bottom flat plan view of the fourth embodiment with parts broken away.

The engaging structure 28 in FIGS. 10 and 11, comprises the crotch area 20 of the garment 14 having two spaced apart triangular openings 56. Opposite ends 29 of the absorbent pad 30 can be inserted through the triangular openings 56 on the interior surface 42 of the crotch area 20. A pair of triangular end pockets 58 are provided. The securing facility 32 will attach each triangular end pocket 58 to the exterior surface 52 of the crotch area 20, adjacent one triangular opening 56. The opposite ends 29 of the absorbent pad 30 extending through the triangular openings 56 in the crotch area 20, will be received and retained within the triangular end pockets 58.

The garment 14 is fabricated out of a cotton fabric 60. The elongated flexible pocket 34 is fabricated out of a nylon fabric 62. The elongated flexible pocket 48 is fabricated out of an elastic nylon fabric 64. Each curved end pocket 54 is also fabricated out of the elastic nylon fabric 64. Each triangular end pocket 58 is also fabricated out of the elastic nylon fabric 64.

LIST OF REFERENCE NUMBERS 12 menstrual underpants
14 garment of 12
16 front portion of 14
18 rear portion of 14
20 crotch area of 14
22 leg opening in 14
24 waist opening in 14
26 woman
28 engaging structure of 12
29 end of 30
30 absorbent pad
32 securing facility
34 elongated flexible pocket of 28
36 rounded end of 34
38 transverse slot opening in 34
40 mating hook and loop pile fastener material for 32
42 interior surface of 20
44 heat seal for 32
46 transverse slot opening of 28 in 20
48 elongated flexible pocket of 28
50 rounded end of 48
52 exterior surface of 20
54 curved end pocket of 28
56 triangular opening of 28 in 20
58 triangular end pocket of 28
60 cotton fabric for 14
62 nylon fabric for 34
64 elastic nylon fabric for 48, 54 and 58

It will be understood that each of the elements described above, or two or more together may also find a useful application in other types of methods differing from the type described above.

While certain novel features of this invention have been shown and described are pointed out in the annexed claims, it is not intended to be limited to the details above, since it will be understood that various omissions, modifications, substitutions and changes in the forms and details of the device illustrated and in its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and desired to be protected by Letters Patent is set forth in the appended claims:

1. A menstrual underpants comprising:

a) a garment configured with a front portion, a rear portion, an inside crotch area having two leg openings and a waist opening, so as to be worn about a lower torso of a woman;

b) an elongated opening in said crotch area having a perimeter on the inside of said garment lined with hook or loop pile fastening material; and c) an elongated pocket having a perimeter and corresponding to the size and shape of said elongated opening said protector having mating loop pile or hook material lining one side thereof for engaging the fastening material along said elongated opening to close said opening along the inside of said garment when worn;

d) said pocket having a pair of spaced transverse slot openings; and e) an elongated absorbent pad having ends inserted into said pocket through said slots for holding said pad in place in the crotch area while said garment is being worn, said pad not moving up and down so that ends of said absorbent pad do not curl up.

2. The menstrual underpants of claim 1 in which said pocket has a heat seal about the perimeter thereof.

3. The menstrual underpants of claim 2 in which said elongated opening and pocket have rounded edges, each of said slots is paced away from a rounded end.

\* \* \* \* \*